United States Patent
Nemes et al.

(10) Patent No.: US 10,813,776 B2
(45) Date of Patent: Oct. 27, 2020

(54) CUSTOMIZABLE INTRALUMINAL BRONCHIAL STENTS AND METHODS FOR SUPPORTING A BRONCHUS USING THE SAME

(71) Applicant: Regents of the University of Minnesota, Minneapolis, MN (US)

(72) Inventors: András Nemes, Deepdene (AU); Robroy MacIver, Minneapolis, MN (US); Filippo Coletti, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 34 days.

(21) Appl. No.: 15/946,901

(22) Filed: Apr. 6, 2018

(65) Prior Publication Data

US 2018/0289515 A1 Oct. 11, 2018

Related U.S. Application Data

(60) Provisional application No. 62/482,789, filed on Apr. 7, 2017.

(51) Int. Cl.
| | |
|---|---|
| A61F 2/88 | (2006.01) |
| A61F 2/04 | (2013.01) |
| A61F 2/94 | (2013.01) |
| B33Y 10/00 | (2015.01) |
| B33Y 80/00 | (2015.01) |

(52) U.S. Cl.
CPC .............. *A61F 2/88* (2013.01); *A61F 2/04* (2013.01); *A61F 2/94* (2013.01); *A61F 2002/043* (2013.01); *A61F 2240/002* (2013.01); *A61F 2250/0082* (2013.01); *B33Y 10/00* (2014.12); *B33Y 80/00* (2014.12)

(58) Field of Classification Search
CPC ........................................................ A61F 2/88
See application file for complete search history.

(56) References Cited

U.S. PATENT DOCUMENTS

| | | | |
|---|---|---|---|
| 2006/0036301 A1* | 2/2006 | Eggers | A61B 18/04 607/103 |
| 2007/0261701 A1 | 11/2007 | Sanders | |
| 2011/0230974 A1 | 9/2011 | Musani | |
| 2018/0289515 A1 | 10/2018 | Nemes | |

FOREIGN PATENT DOCUMENTS

| | | |
|---|---|---|
| EP | 0177330 | 6/1991 |
| WO | WO 2009/042657 | 4/2009 |

OTHER PUBLICATIONS

Application and Filing Receipt for U.S. Appl. No. 16/293,247, filed Mar. 5, 2019, Inventor: Landaeta et al.

* cited by examiner

*Primary Examiner* — Matthew W Schall
(74) *Attorney, Agent, or Firm* — Patterson Thuente Pedersen, P.A.

(57) ABSTRACT

Embodiments relate to stents for supporting an airway or other duct or plenum. The stents can be rapidly customized and inserted into the airway, obviating the need for subsequent intubation or for invasive procedures.

6 Claims, 13 Drawing Sheets

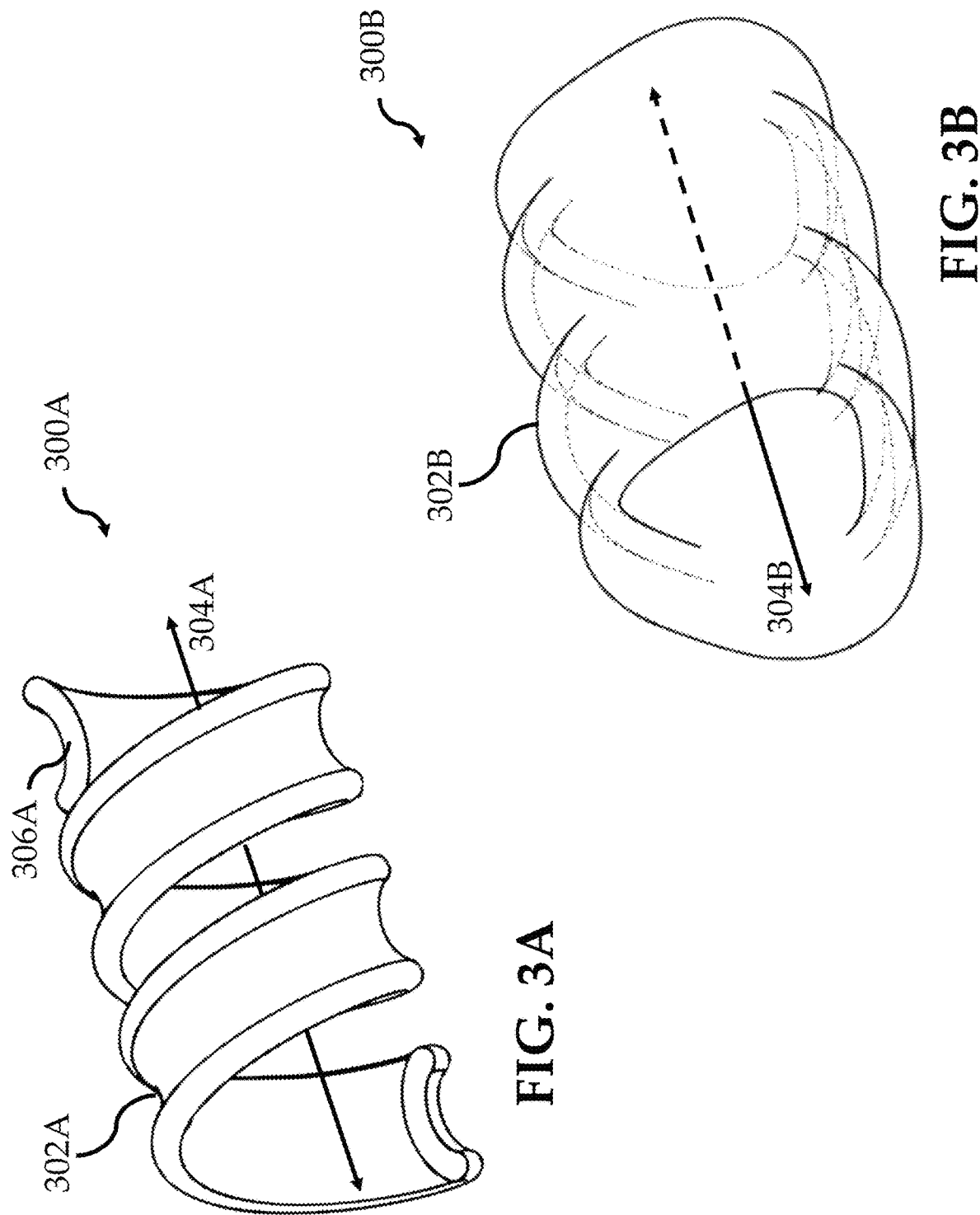

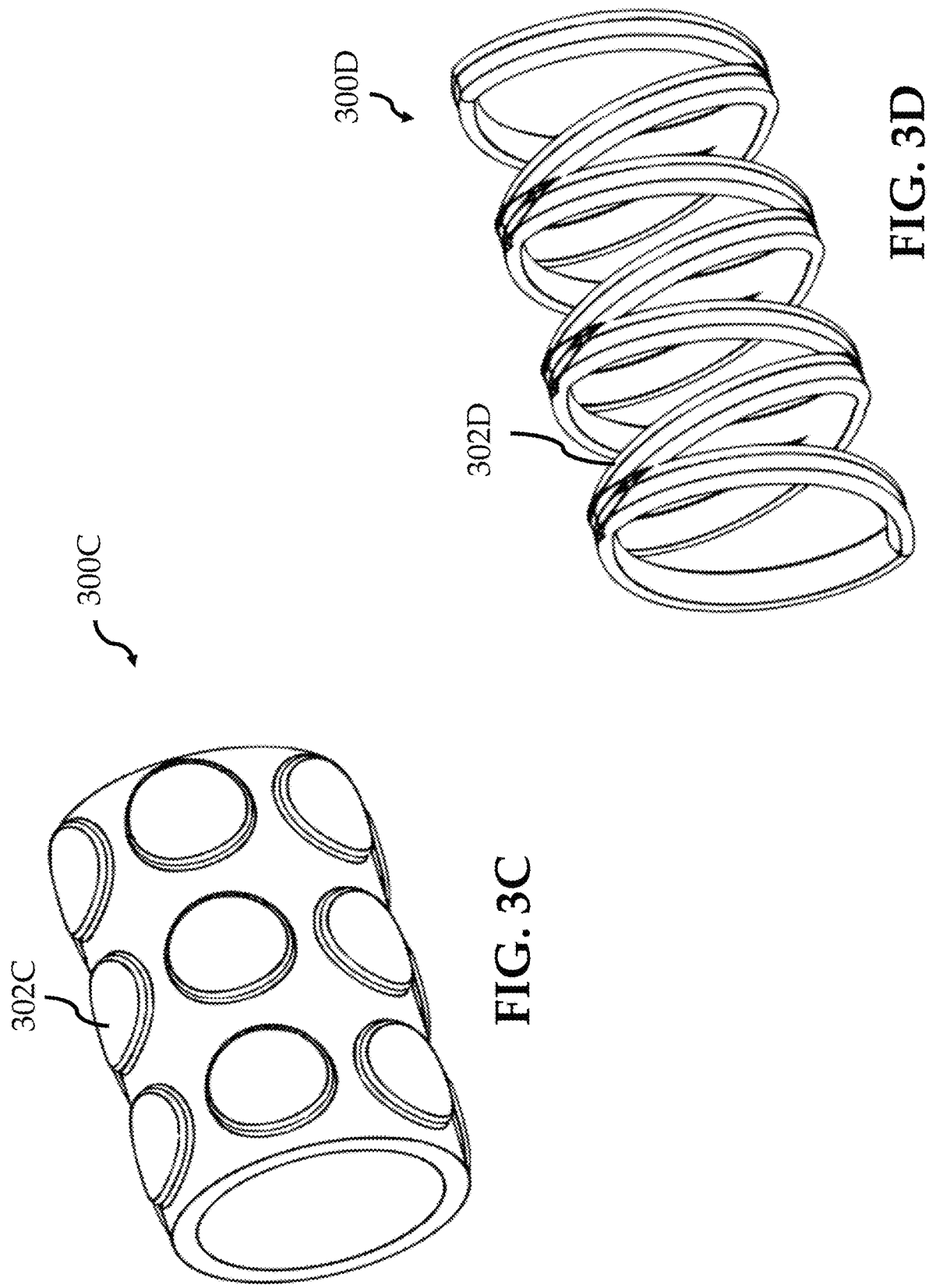

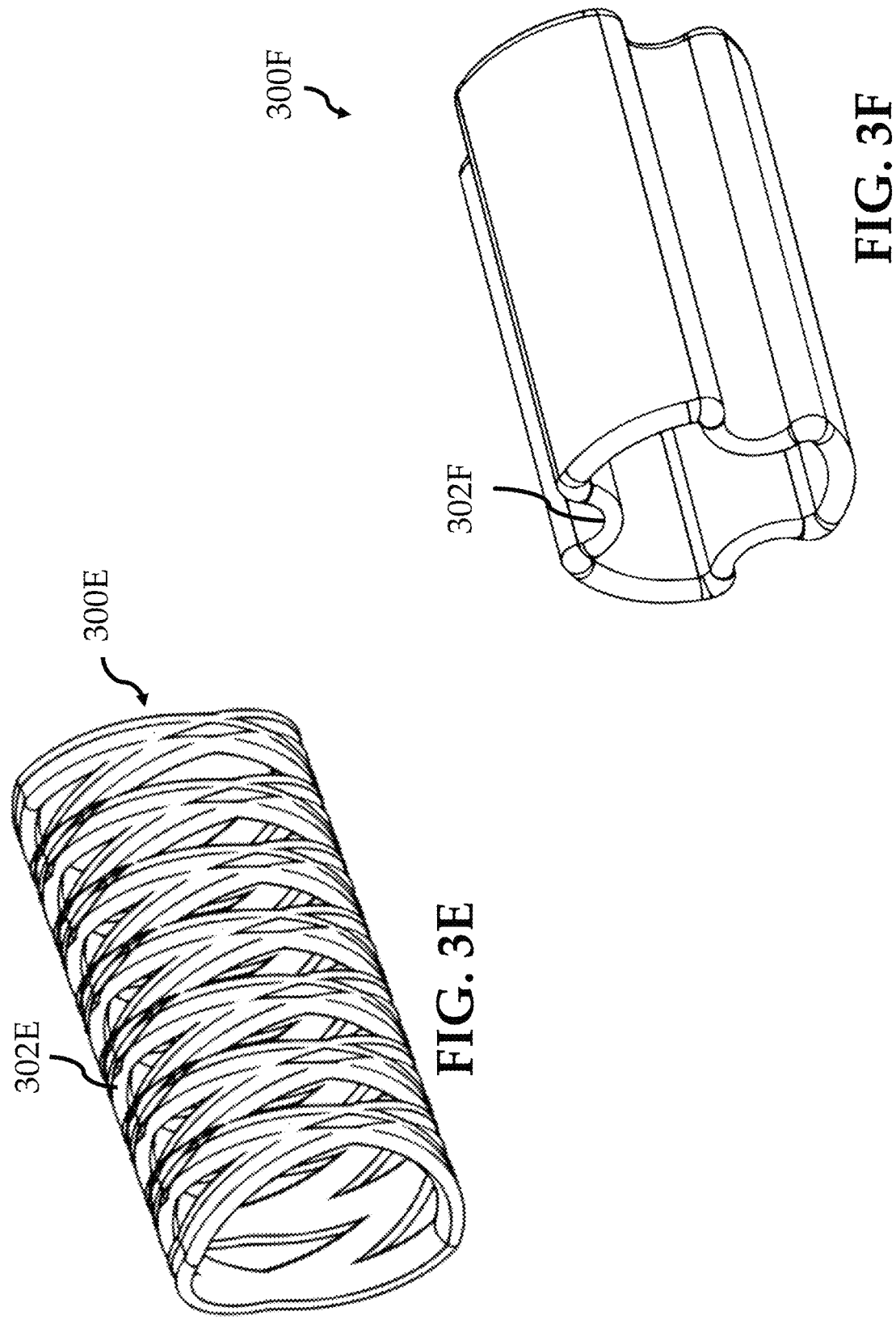

CUSTOMIZABLE INTRALUMINAL BRONCHIAL STENTS AND METHODS FOR SUPPORTING A BRONCHUS USING THE SAME

RELATED APPLICATION

The present application claims the benefit of U.S. Provisional Application No. 62/482,789, filed Apr. 7, 2017, which is hereby incorporated herein in its entirety by reference.

TECHNICAL FIELD

Embodiments relate to devices providing patency to, or preventing collapse of, tubular structures of the body such as the bronchi or trachea.

BACKGROUND

Tracheo-bronchomalacia (TBM) is a condition in which patients, typically children, can suffer from collapse of the trachea and/or bronchi. The disease is characterized by soft airways, which are prone to collapse. TBM is particularly dangerous to children, because their airways are relatively small and even minor sources of pressure such as a nearby blood vessel can impinge or collapse the airway.

Whole regions of the lung of a patient with TBM can be poorly ventilated and, due to compression of the airways, airway secretions that are normally cleared cause frequent respiratory infections and can necessitate positive pressure ventilation. As a result, children with TBM suffer from significant morbidity and mortality rates.

Conventional medical therapy involves chronic nebulizer treatments that break up mucous plugs that form secondary to decreased airway size. Frequent respiratory infections are also common leading to multiple episodes of antibiotics. Treatment often is palliative with expectorants and/or placement of a tracheostomy to artificially elevate airways pressures to a point where the airways no longer collapse. Complications of tracheostomies can be numerous and the cost of home ventilator care is high.

Surgical treatment involves artificially stenting open the airways by a procedure in which the overlying soft tissue is pulled away from the airway and is fixed to the chest wall or an artificial strut placed around the airway. Often the side effects of treatment can include morbidity rates similar to that of TBM itself. Many children suffering from TBM also have many other comorbidities. Caregivers for these children have their lives severely affected by having to do complex respiratory treatments. If the child is ventilated, he or she may have to be taken out of the home during convalescence.

Stents may be inserted into tracheae or bronchus to treat TBM. Although a stent placed inside the trachea or bronchus would be better to prevent collapse of the airway, conventional stents are not suitable for placement there. Silicon stents that are usable for treatment of TBM in adults generally have walls that are too thick, such that if they were scaled down in diameter for use in children they would leave little or no passageway for air to the lungs. Metal expandable stents may have a thinner wall, but they also have a high in-growth rate. Therefore, they can be difficult or impossible to later remove. As the child grows, therefore, the airway would remain the same size, which may be insufficient.

Some existing stents are made of metal coated in silicone. These stents are currently not available in any size that is appropriate for children. Variations in length and diameter of airways make sizing stents difficult. Inadequately sized stents can lead to migration and/or obstruction in the airway.

Over time, the symptoms of TBM may become less pronounced as the trachea grows wider and becomes less pliable. Therefore, there is a need for a treatment for TBM in children that can prevent airway collapse without the adverse effects of intubation or tracheal stents.

SUMMARY

In one embodiment, a stent includes a conformable body extending along a length. At least one ridge extends along an outer wall of the conformable body. At least one engagement feature is arranged along an inner wall of the conformable body configured to engage with an adjacent component to advance the stent. The stent comprises a material that is conformable, biocompatible, and suitable for additive manufacturing.

In another embodiment, a system includes a guidewire, a stent having a conformable body extending along a length and defining an outer wall and an inner wall at outer and inner diameters, respectively. The outer wall defines a ridge. The system includes an applicator configured to removably engage with the inner wall of the stent, the applicator defining a channel for the guidewire. The system further includes a driver mechanically coupled to the applicator such that rotational manipulation of the driver causes a corresponding longitudinal movement of the stent.

In another embodiment, a method includes measuring a diameter of an airway, determining a set of features of a stent corresponding to the diameter of the airway, creating the stent having the set of features, assembling a system comprising the stent, an applicator, a guidewire, and a driver, advancing the stent to a position in the airway by advancing a guidewire to the position in the airway and rotating the driver to cause a corresponding longitudinal movement of the stent until the stent has advanced to the position, and removing the applicator, guidewire, and driver while the stent remains at the position.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 3A-3G are perspective views of stents according to embodiments.

Figure 1A:
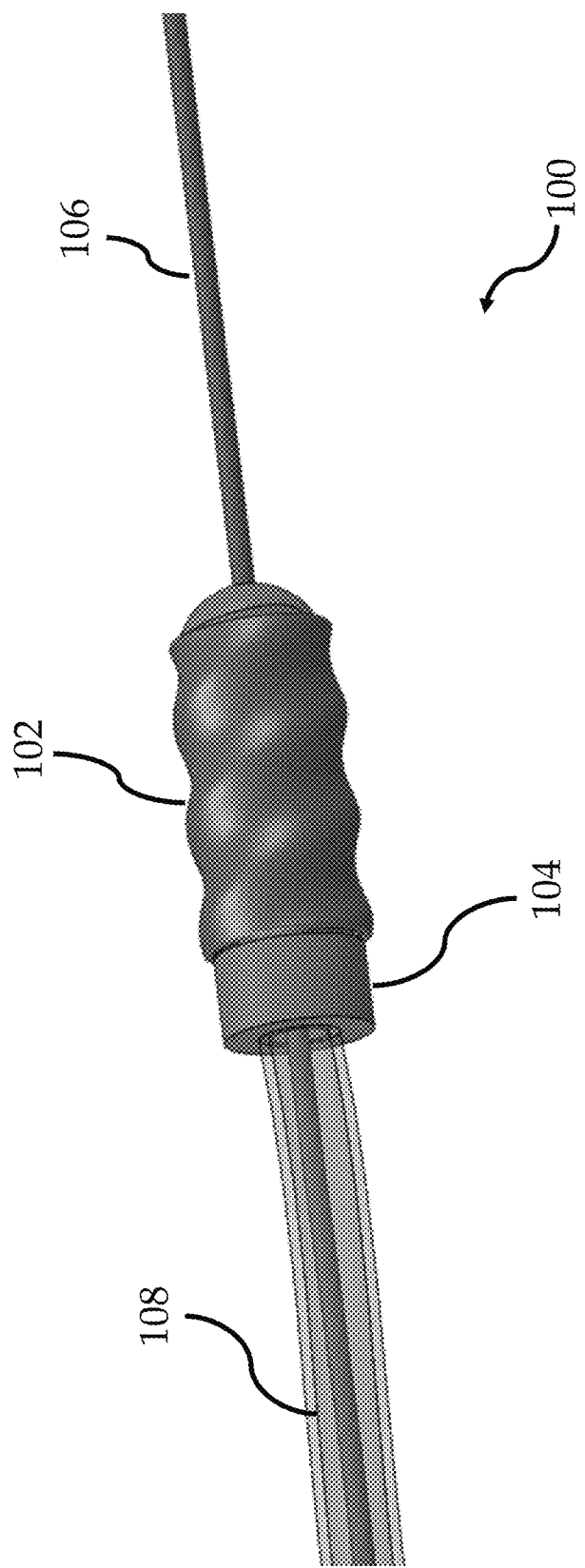
FIG. 1A is a perspective view of a system for treatment of an airway according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments described herein include stents for use in treatment of tracheo-bronchomalacia (TBM). According to embodiments described herein, customized stents can be effectively and precisely deployed, and are suitable for use in the small airways of children and infants. These stents can be deployed inside the airway, rather than using a "pexy" procedure in which a stent is attached to the outside of an airway, which improves airway collapse resistance. Furthermore, the stents can be deployed rapidly using a four-part system including a guide-wire, a driver, an applicator, and the stent.

FIG. 1A is a perspective view showing a system 100 for treating TBM according to an embodiment. System 100 includes a stent 102, an applicator 104, a guidewire 106, and a driver 108. System 100 can deliver stent 102 to a position within the airway of a patient to provide support against collapse due to TBM or some other condition.

Stent 102 is a device that can prevent collapse of an airway. Stent 102 can be customized to a desired dimension or shape. In embodiments, stent 102 can be sized to correspond to an airway of a particular patient, have a driving screw shape or other external features to improve retention in the patient's airway, and can be made of materials that have desired strength properties, can be used in rapid prototyping, and are biocompatible or bioabsorbable. In embodiments, stent 102 can also include a lubricious coating or a layer of lubricant can be applied to a wall of stent 102.

Stent 102 can be sized such that it will provide support to the inner wall of an airway. In embodiments, stent 102 is made of a conformable material that compresses or deforms when pressure is applied to it. Stent 102 can be formed such that its uncompressed size is about 10% greater than the natural resting position of the airway, or in alternative embodiments stent 102 can have an uncompressed size that is about 20% greater than the natural resting position of the airway. In alternative embodiments, stent 102 can be larger or smaller relative to the airway in order to ensure that stent 102 will not move due to regular respiration or coughing, and will provide a desired level of support for the airway.

As shown in the embodiment of FIG. 1A, stent 102 has a driving screw shape. A driving screw shape as shown in FIG. 1A facilitates deployment in the airway of a patient. During delivery of stent 102 to a desired portion of the airway, stent 102 can be rotated to advance in the airway even where a snug fit exists.

Figure 1B:
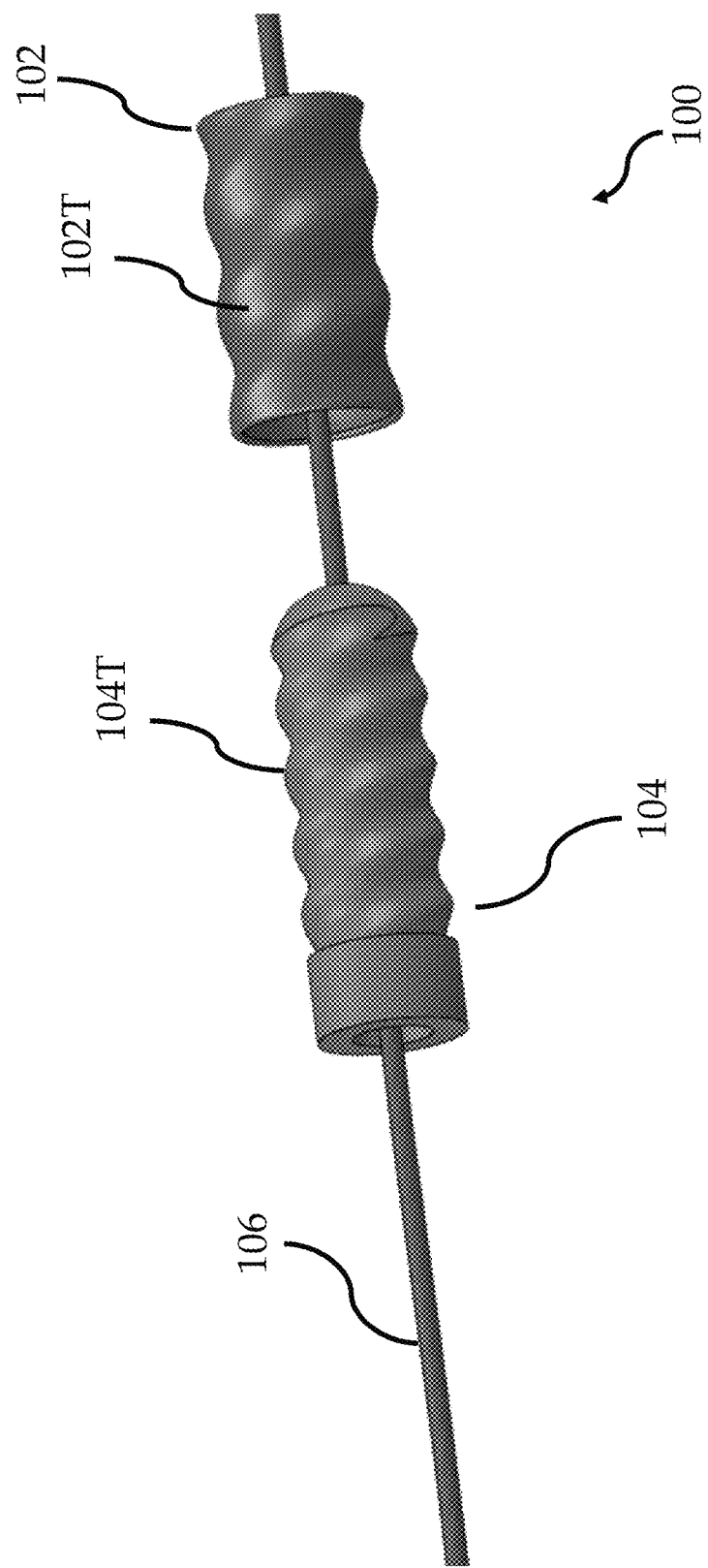
FIG. 1B is a perspective view of the guidewire, applicator, and stent of the system of FIG. 1A.

Stent 102 can be made of a variety of materials. In embodiments, stent 102 can be a silicone-based or other flexible polymer. For customizable stents 102, it may be desirable to make stent 102 from a material that can be used as the feedstock for an additive manufacturing process. In embodiments, stent 102 can be made from a polymer usable in stereolithography, continuous liquid interphase printing, or selective laser sintering. In addition, in embodiments stent 102 is made of a biocompatible material Stent 102 has a radially inner surface that is configured to engage with applicator 104, in the embodiment shown in FIG. 1A. Applicator 104 is engaged with stent 102. FIG. 1B more clearly shows the engaging mechanical features of stent 102 and applicator 104. Applicator 104 has threads 104T such that as it is rotated in a first direction, it drives into stent 102. Stent 102 can include radially inner features (not shown) that engage with threads 104T, in embodiments, or alternatively can simply be conformable such that threads 104T drive into and engage with stent 102. Stent 102 likewise includes threads 102T such that as it is rotated in the first direction, it will advance axially, away from applicator 104. As a result, system 100 can be used to drive stent 102 to a desired position, and applicator 104 can subsequently be reversed out of stent 102 and removed from the airway.

In alternative embodiments, threads 104T could be replaced by some other engagement feature. For example, applicator 104 could include a spline, keyed structure, or other engagement feature through which applicator 104 can drive stent 102 to a desired portion or remove stent 102 from that position if it needs to be replaced.

When applicator 104 is backed out of stent 102, as shown in FIG. 1B, the hollow inner portion of stent 102 permits passage of air therethrough. In embodiments, the radially inner portion of stent 102 is also cleanable using applicator 104 or a similar structure to break apart and remove buildup.

Guidewire 106 can be used to route system 100 to a desired position. Guidewire 106 is flexible and can pass through the airway to set forth the pathway along which the rest of system 100 is later delivered. Driver 108 can be positioned around guidewire 106, as shown in FIG. 1A, or in alternative embodiments guidewire 106 could run parallel to driver 108. Both stent 102 and applicator 104 are arranged guidewire 106. Guidewire 106 can extend into the airway a predetermined distance under the control of a medical professional. In embodiments, guidewire 106 can be stiff enough to facilitate tracking of a deployment device such as applicator 104.

In the embodiment shown in FIG. 1A, driver 108 is a microcatheter. In embodiments, using a microcatheter as driver 108 is advantageous because a standard bronchoscope can then be used to deliver system 100. Furthermore, as described previously, a microcatheter can be used as driver 108 while guidewire 106 is positioned coaxially within the microcatheter. This prevents winding of guidewire 106 and driver 108 as applicator 104 is rotated to drive stent 102.

In embodiments, driver 108 can be squeezed by applicator 104. Driver 108 can be secured to applicator 104 by addition of a device that allows for rotationally increased torque on applicator 104 such that eventually rotation of driver 108 causes an accompanying rotation of applicator 104. As shown in FIG. 1A, driver 108 is mechanically coupled to applicator 104, and applicator 104 is coupled to stent 102, which has a screw-like shape, such that rotational manipulation of driver 108 can cause a corresponding longitudinal movement of the stent. Due to the threaded nature of the stent 102 and applicator 104 (as shown in more detail in FIG. 1B), rotation of driver 108 in a first direction causes stent 102 to advance. In contrast, rotation of driver 108 in the opposite direction causes applicator 104 to back out of stent 102, provided that stent 102 is held by a surrounding structure such as an airway.

Figure 2:
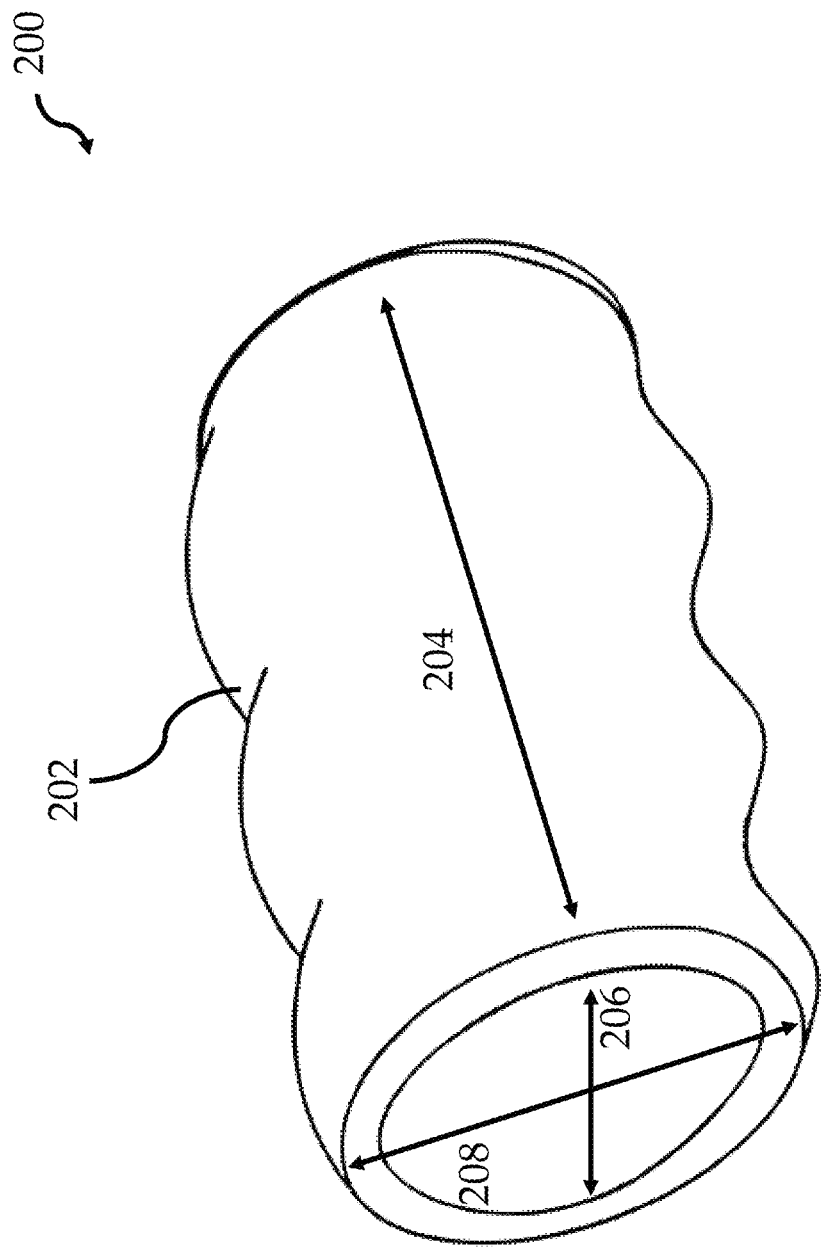
FIG. 2 is a perspective view of a stent according to an embodiment.

FIG. 2 is a perspective view of a stent 200 including ridges 202. Stent 200 has a length 204, an inner diameter 206, and an outer diameter 208. In embodiments, stent 200 can be used in a system (e.g., system 100 of FIGS. 1A and 1B) for treating TBM.

Ridges 202 can be used for at least two purposes. First, as previously described with respect to FIGS. 1A and 1B, ridges 202 can be used to drive stent 200 into an airway. Where stent 200 is in contact with the airway, rotation of a threaded stent 200 having inclined ridges 202 can be used to provide a driving force. Additionally or alternatively, ridges 202 can have pitch or spacing that is configured to match with the contours of a patient's airway.

As noted previously, stent 200 can be additively manufactured. Using additive manufacturing allows stent 200 to be customized to the particular airway of the patient in which it will be placed. In embodiments, a physician or other medical professional can determine the spacing of cartilage rings that are found along the length of a trachea. Ridges 202 can then be spaced at intervals configured to coincide with those cartilage rings. As such, stent 200 is more securely positioned within the trachea, and less likely to become dislodged during normal usage.

Additive manufacturing also allows for production of alternative embodiments of stent 200 that conform with the airway of a particular patient in other ways. For example, in embodiments a portion of the airway that is subject to collapse may be in a curved section of the airway, or an area that is relatively narrower at one part than at another. Such variations can be incorporated into the design of stents such as stent 102 of FIGS. 1A and 1B or stent 200 of FIG. 2.

Stent 200 has a length 204, an inner diameter 206, and an outer diameter 208. In various embodiments length 204, inner diameter 206, and outer diameter 208 can be customized for a particular patient. Based upon measurements of the airway, length 204, inner diameter 206, and outer diameter 208 can be selected to provide support for an airway, create a sufficiently-large cross-sectional area for airflow in a portion of the airway affected by TBM, and remain engaged with the airway to prevent displacement or movement of stent 200.

Length 204 can be selected based upon the length of an airway such as a trachea or bronchus, for example. In some embodiments, length 204 corresponds to the length of a portion of an airway that is likely to become obstructed or impinged. For a patient suffering from TBM, this may be a portion of the airway that is adjacent to a vein or artery, for example.

Inner diameter 206 can also be customized to a particular patient. Inner diameter 206 determines the cross-sectional area for airflow. Inner diameter 206 is the distance across stent 200 at a radially inner wall. For smaller patients such as infants and children, inner diameter 206 may be relatively smaller than the inner diameter 206 necessary for adults or larger patients. Inner diameter 206 may vary along length 204. For example, in embodiments stent 202 can include radially inner engagement features (not shown) which are configured to engage with counterparts on an applicator (e.g., threads 104T of applicator 104 as shown in FIG. 1B).

In embodiments, inner diameter 206 varies depending on the position within stent 200. For example, in any given cross-section there may be a major axis having a relatively larger inner diameter 206 and a minor axis having a relatively smaller inner diameter 206.

Outer diameter 208 can also be customized to a particular patient. As described previously with respect to FIGS. 1A and 1B, stent 200 engages with an airway in which it is positioned. Outer diameter 208 is the distance across stent 200 at a radially outer wall. Outer diameter 208 is generally as large as or slightly larger than the inner diameter of an airway in which it is housed. In embodiments, outer diameter 208 varies along length 204. For example, in embodiments stent 200 includes ridges 202 which have a relatively larger outer diameter 208 compared with the remainder of stent 200. In embodiments, other features can affect outer diameter 208, such as outwardly-extending flanges or ridges 202 that are configured to engage with cartilaginous features of the airway.

In embodiments, outer diameter 208 varies depending on the position within stent 200. For example, in any given cross-section there may be a major axis having a relatively larger outer diameter 208 and a minor axis having a relatively smaller outer diameter 208.

FIG. 3A is a perspective view of a stent 300A according to another embodiment. Stent 300A of FIG. 3A is shaped as a helical coil. Stent 300A extends along length 304A and, like stent 102 of FIGS. 1A and 1B as well as stent 200 of FIG. 2, is configured to be rotated by a counterpart applicator (not shown) such that it will move along an airway. Once the applicator is removed, stent 300A provides support for the airway but does not cover the entirety of the inner portion of the airway along length 304A. Inverse ridges 302A can engage with cartilage or other features of the airway to prevent movement undesired movement of stent 300A after it has been positioned in the airway.

In embodiments, stent 300A can include soft edge 306A. Soft edge 306A is blunted and/or curved in order to prevent damage to the surrounding tissue as stent 300A is advanced. Similar structures can be present at a leading edge of stent 102 of FIGS. 1A and 1B, or a leading edge of stent 200 of FIG. 2. Furthermore, as depicted in FIGS. 1A and 1B, an applicator such as applicator 104 can include a rounded or blunted end that extends past stent 102 during deployment of the stent.

FIG. 3B is a perspective view of a stent 300B according to yet another embodiment. Stent 300B includes ridges 302B which are configured to engage with a feature of the airway such as cartilage. Unlike previously-described embodiments, stent 300B does not have a screw-like shape to ridges 302B. Stent 300B prevents collapse or impingement of an airway due to TBM or similar conditions along its length 304B.

FIG. 3C is a perspective view of a stent 300C according to yet another embodiment. Stent 300C includes a series of bumps 302C that are configured to engage with an airway to prevent movement of stent 300C therein. Though bumps 302C are depicted as being substantially circular in FIG. 3C, bumps 302C can have another shape (e.g. oval, square, triangular) or comprise bumps of a plurality of different shapes in other embodiments.

FIG. 3D is a perspective view of a stent 300D according to yet another embodiment. Stent 300D includes interwoven helical coils 302D. Stent 300D is similar to similar to stent 300A of FIG. 3A, except that it includes interwoven helical coils rather than a single helical coil. Stent 300D can provide additional structural support as compared to a single helical coil stent 300A, which can prevent collapse of a surrounding airway when deployed.

FIG. 3E is a perspective view of a stent 300E that includes double interwoven helical coils, according to yet another embodiment. Like stent 300D of FIG. 3D, stent 300E of FIG. 3E provides additional support for an airway as compared to a single helical coil embodiment like that shown in FIG. 3A.

FIG. 3F is a perspective view of a stent 300F that is expandable upon delivery. A corresponding applicator (not shown) can deliver stent 300F to an affected portion of an airway, after which flexible or compressible ribs 302F can be used to expand stent 300F. Ribs 302F can also provide clearance around the radial exterior of stent 300F for fluids.

Figure 3G:
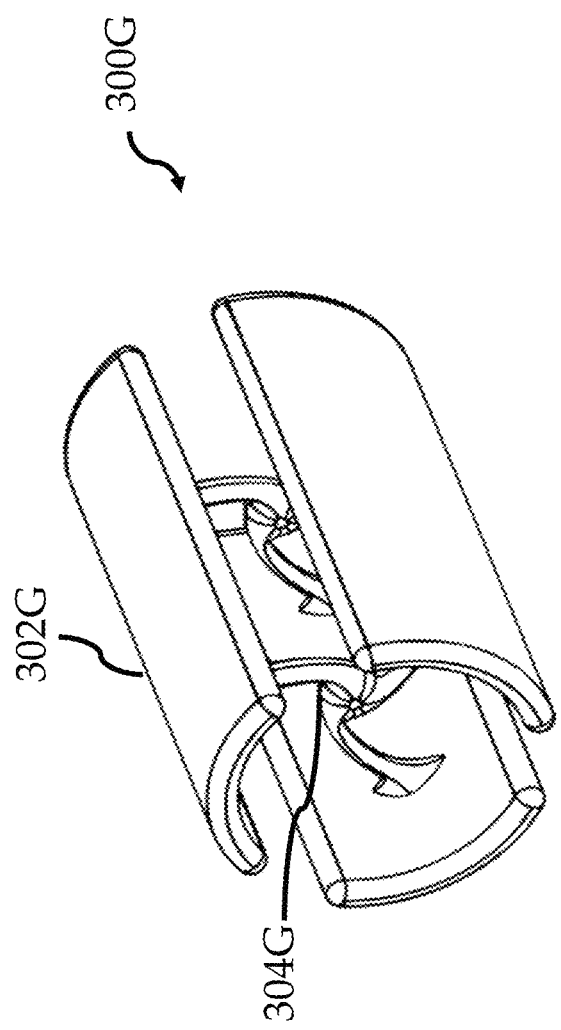

Similarly, FIG. 3G shows an expandable stent 300G. Expandable stent 300G can be used to provide support to an airway from pads 302G, which are pushed radially outward by central spring structures 304G. Stent 300G can be delivered to an affected portion of the airway while in a collapsed state in which the pads 302G are compressed together. In the expanded state as shown in FIG. 3G, gaps are present between pads 302G. Such gaps provide clearance for fluids.

Figure 4A:
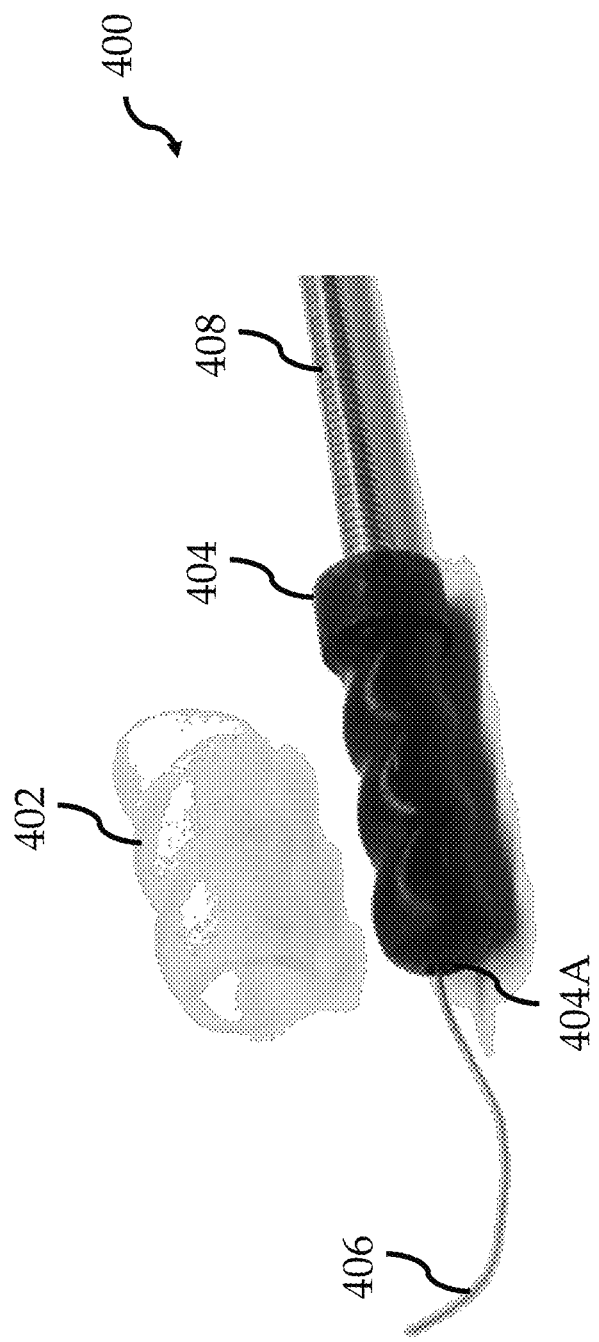
FIGS. 4A and 4B are perspective views of a system for treatment of an airway according to an embodiment.

FIG. 4A is a perspective view of a system 400 including a stent 402, applicator 404, guidewire 406, and driver 408 according to an embodiment. As shown in FIG. 4A, stent 204 is not positioned on applicator 404. Applicator 404 includes a front aperture 404A through which guidewire 406 can be routed through an airway. Driver 408 is hollow in the embodiment shown in FIG. 4A, and guidewire 406 is routed through the center of driver 408.

Figure 4B:
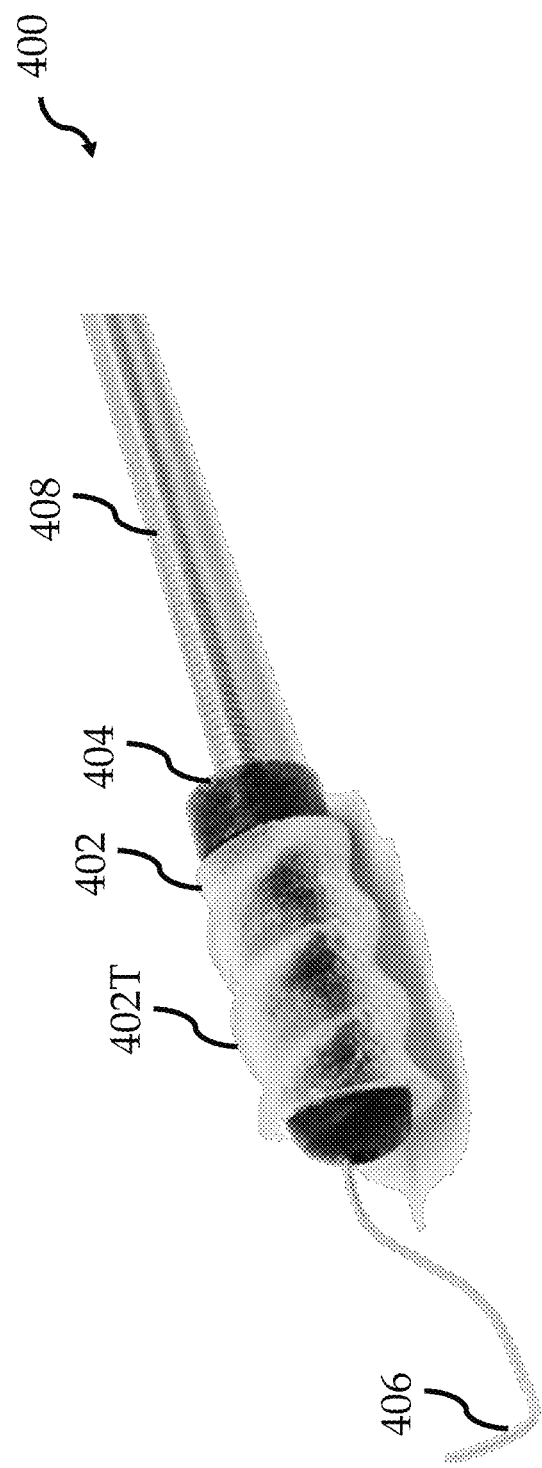

FIG. 4B is a perspective view of the system 400 of FIG. 4A, in which stent 402 is engaged with applicator 404. Driver 408 can rotate applicator 404, which in turn drives stent 402. Threads 402T on stent 402 cause longitudinal movement of system 400 when driver 408 is rotated.

The embodiments described herein are customizable, easy to deliver, and easy to maintain. A screw-like arrangement of threads or ridges can be provided on the exterior of the stent to facilitate forward movement of the stent in an airway when the stent is rotated. Threads or other engagement features on the interior of the stent facilitate engagement with an applicator that can drive the stent to the desired position, after which the applicator can be removed quickly. This arrangement permits for rapid and simple installation without requiring long-term blockage of the airway. Customizable stents permit for arrangements of ridges or threads that will engage with cartilage or other features of the particular airway or each patient.

Polymeric materials that are compressible, suitable for additive manufacturing processes, and compressible can be used in the interior of the airway. For example, in one embodiment a low-durometer silicone urethane material can be used that can be additively manufactured, and is biocompatible and tear-resistant. Such embodiments are gentle on the trachea during installation and are highly pliable.

Alternatively, embodiments can include materials having higher radial strength than silicone-based materials, as well as exhibiting less softening due to exposure to body heat. For example, polymers comprising dioxanone at various hardnesses can be used, which exhibit extended strength retention and flexibility. In still other embodiments, block copolymers of lactide, trimethylene carbonate, and caprolactone were found to exhibit flexibility and strength necessary to prevent collapse of the stent (e.g., 102) and less softening with heat as compared to silicone-based embodiments. In still further embodiments, copolymers of caproprene and glycolide were found to provide desirable material properties for strength and flexibility.

It should be understood that these examples are not limiting, and that other materials could be additively manufactured that provide a desired level of strength, even at body temperature and other environmental conditions (such as moisture, movement, and air flow) found in a trachea. In some embodiments, such as the copolymers described above, the material can be bioabsorbable rather than simply biocompatible. This may be a benefit if some tissue ingrowth into the material is possible. In that event, the stent (e.g., 102) would stay in place, and be gradually absorbed by the body. The stent (e.g., 102) would then not need to be removed, in some embodiments.

Figure 5:
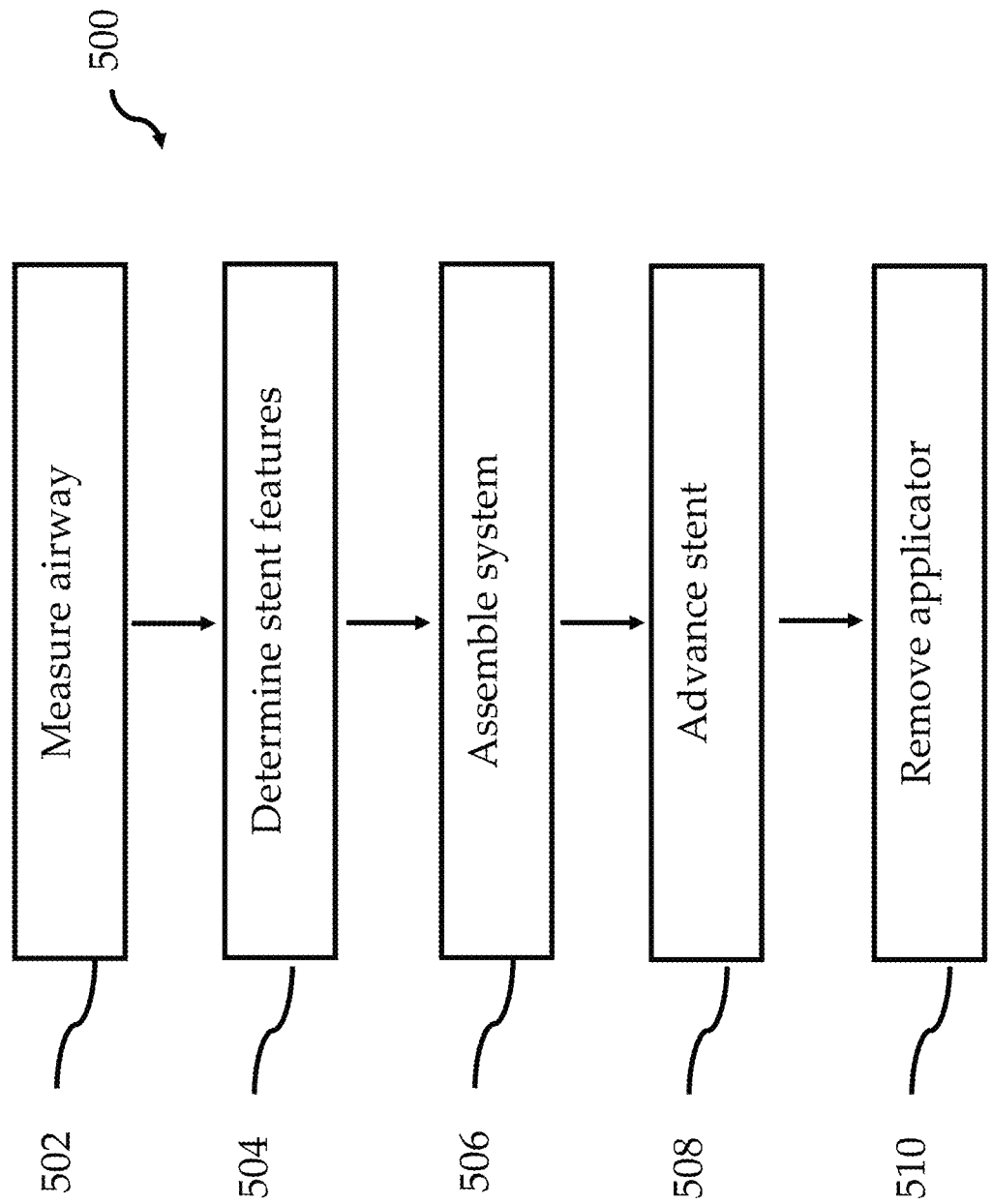
FIG. 5 is a flowchart of a method according to an embodiment.

FIG. 5 is a flowchart of a method 500 for treating TBM, according to an embodiment. The method 500 could be used to treat other disorders, in alternative embodiments, in which providing support for a plenum or similar structure is desired.

At 502, an airway is measured. The airway of a patient suffering from TBM can be measured using dynamic or "breathing" computed tomography (CT) scan, sometime also referred to as a 4DCT scan. Alternatively, the airway can be measured using magnetic resonance imaging (MRI). Airway measurement 502 can provide an indication of the range of diameter of the airway, including a minimum and maximum diameter of the airway.

At 504, stent features are determined. As previously described with respect to other embodiments, it may be beneficial to produce a stent having an outer diameter that is greater than the maximum diameter of the airway. In this way, the stent remains engaged at all times and is not likely to come loose during coughing or regular respiration. In addition to outer diameter, the inner diameter of the stent can be determined such that a desired wall thickness is created that will have sufficient strength to keep the airway from collapsing, while remaining sufficiently large to allow the patient to breathe through it comfortably.

In addition to the inner diameter, outer diameter, and length of the stent, external features can be determined at 504. Such internal features, as previously described, can be used to provide a screw-like external contour to the stent so that it can be advanced to a desired portion of the airway, in embodiments. Alternatively or additionally, engagement features on the exterior of the stent can be added such that the stent will engage with cartilage or other features of the airway, in embodiments, to prevent undesired movement of the stent.

Furthermore, materials can be selected at 504. The material features of the stent can be selected such that they can be rapidly prototyped and customized to the patient as described above, as well as having sufficient strength to prevent collapse of the airway. Finally, in embodiments the material may be chosen so that it is biocompatible.

A system is assembled at 506. The system can include a stent, an applicator, a guidewire, and a driver, in embodiments. In some embodiments, the driver and applicator can be a single component, whereas in other embodiments they are separate components. The stent can be driven rotationally by the applicator.

At 508, the stent is advanced. In embodiments, the rotation of an applicator of the system causes rotation of the stent. The stent, likewise, can be threaded such that rotation of the stent causes the stent to advance or retreat in the airway. The applicator can therefore be manipulated until the stent is in a desired position.

At 510, the applicator is removed, leaving the stent in the desired position of the airway. Unlike existing stents recently devised for children with tracheo-broncomalacia, which are placed outside of the airway and tether the airway tissue, the proposed device will be inserted in the bronchial tree by bronchoscopic means. This approach provides stronger support against lumen collapse, facilitated by a stent that is thin-walled and flexible to limit the invasiveness of insertion.

Figure 6C:
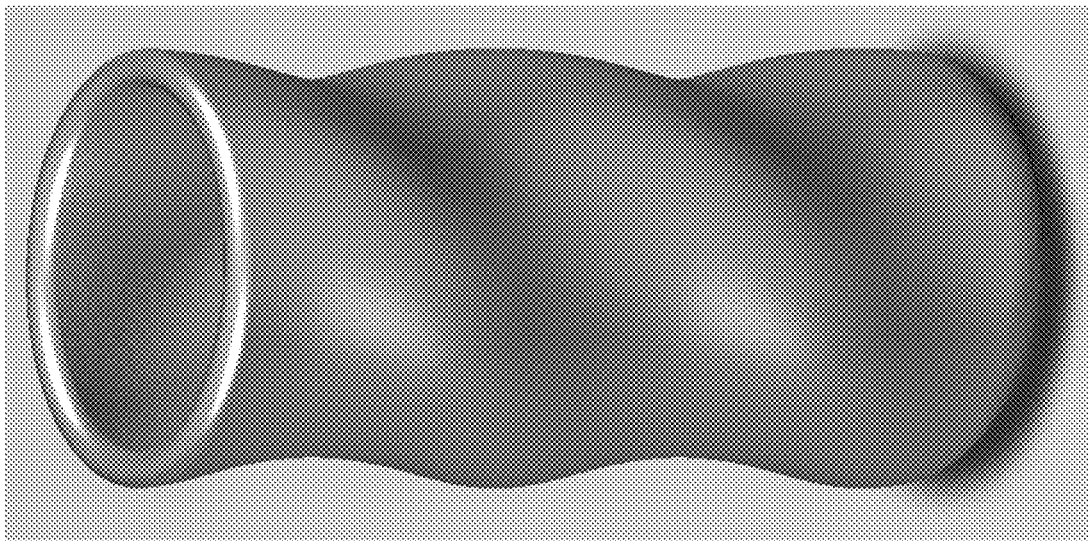
FIGS. 6A-6C are perspective views of three stents according to embodiments.
Figure 6B:
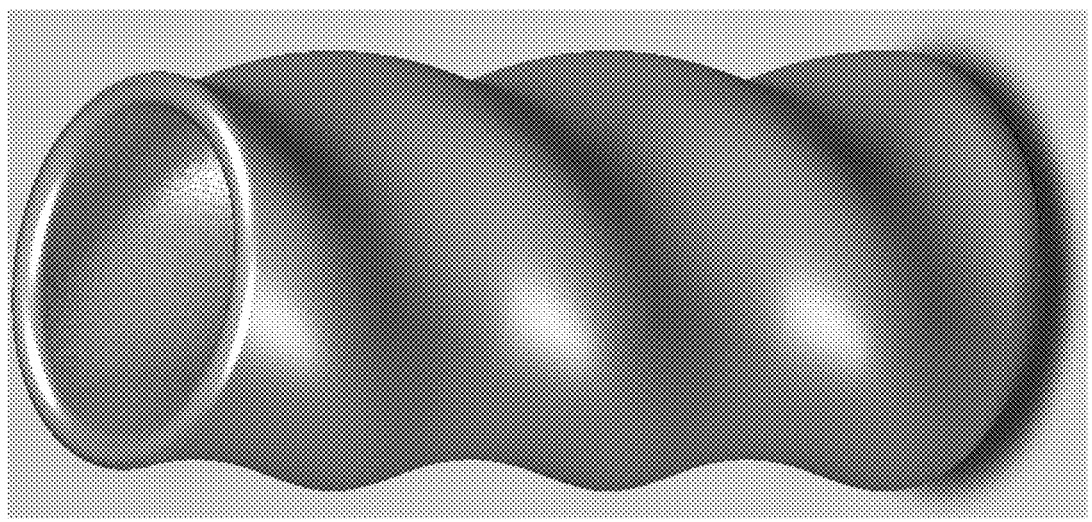
Figure 6A:
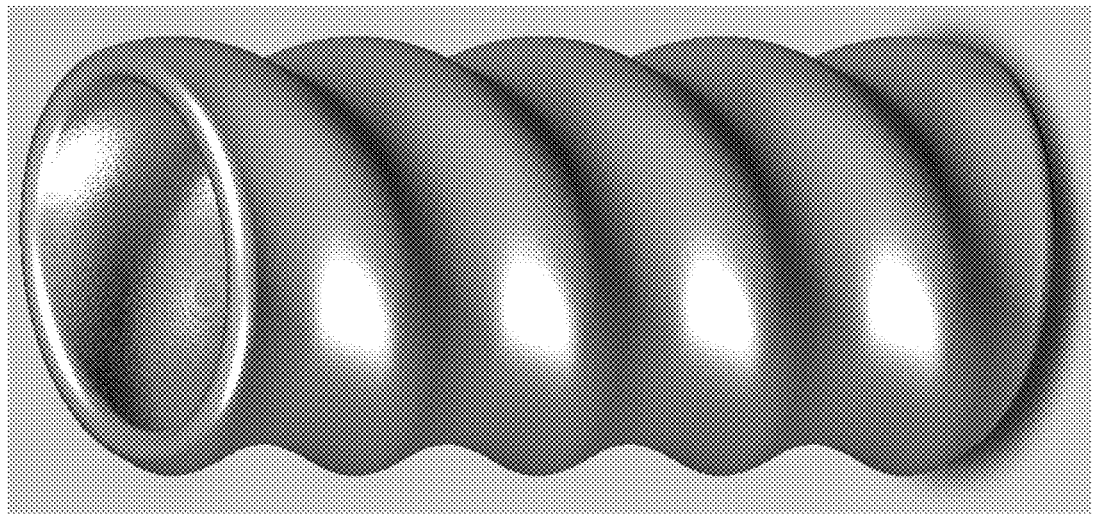
Figure 7A:
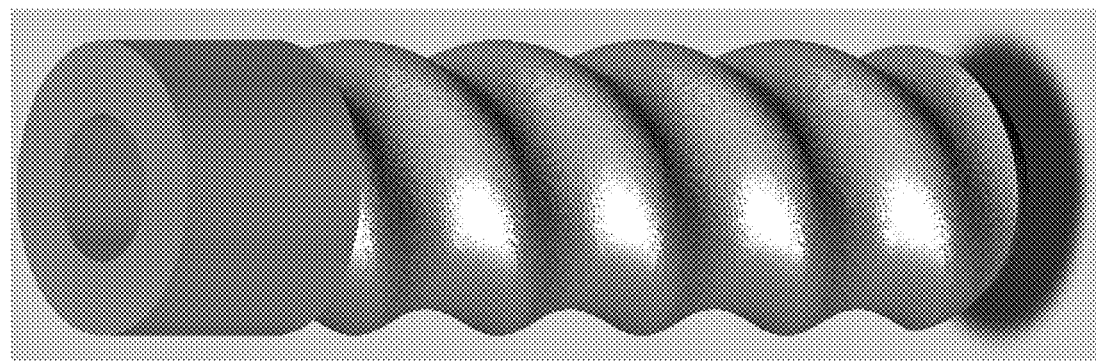
FIGS. 7A-7C are perspective views of three applicators according to embodiments.
Figure 7B:
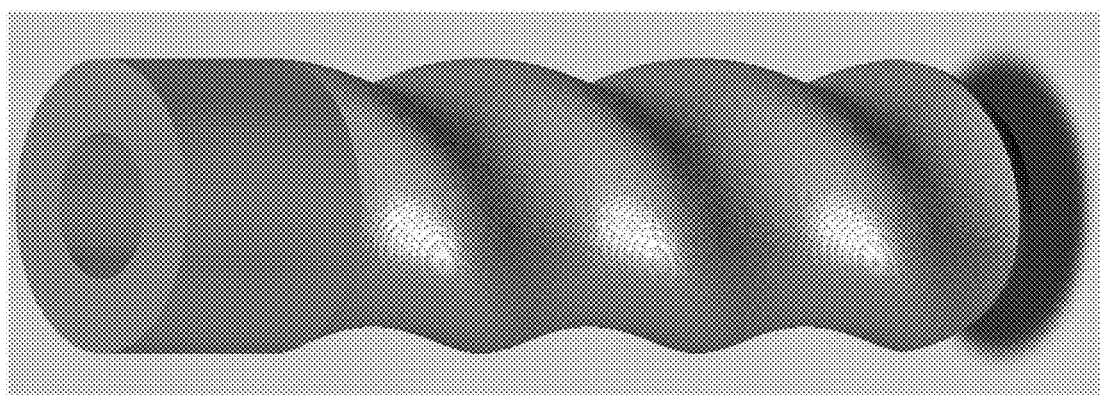
Figure 7C:
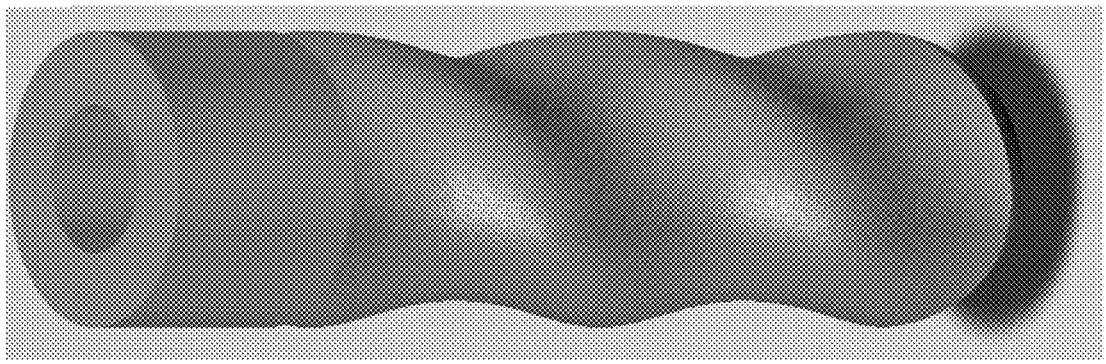

FIGS. 6A, 6B, and 6C show three example embodiments of stents that could be used in various embodiments. The stent of FIG. 6A has a relatively higher thread rate than the stent of FIG. 6B, which in turn has a higher thread rate than the stent of FIG. 6C. FIGS. 7A, 7B, and 7C show three corresponding applicators, which are configured to interact with the stents of FIGS. 6A, 6B, and 6C, respectively. The thread rates of the applicators also is highest in FIG. 7A, lower in FIG. 7B, and lowest in FIG. 7C. In alternative embodiments, the thread rate of the exterior of the stents (e.g., the stents of FIGS. 6A-6C) need not match or even be proportional to the thread rates on the interior of those same stents. That is, a stent having a relatively low exterior thread rate (such as the one shown in FIG. 6C could nonetheless have a relatively high interior thread rate (configured to engage with an applicator such as the one shown in FIG. 7A), or vice versa.

Figure 8:
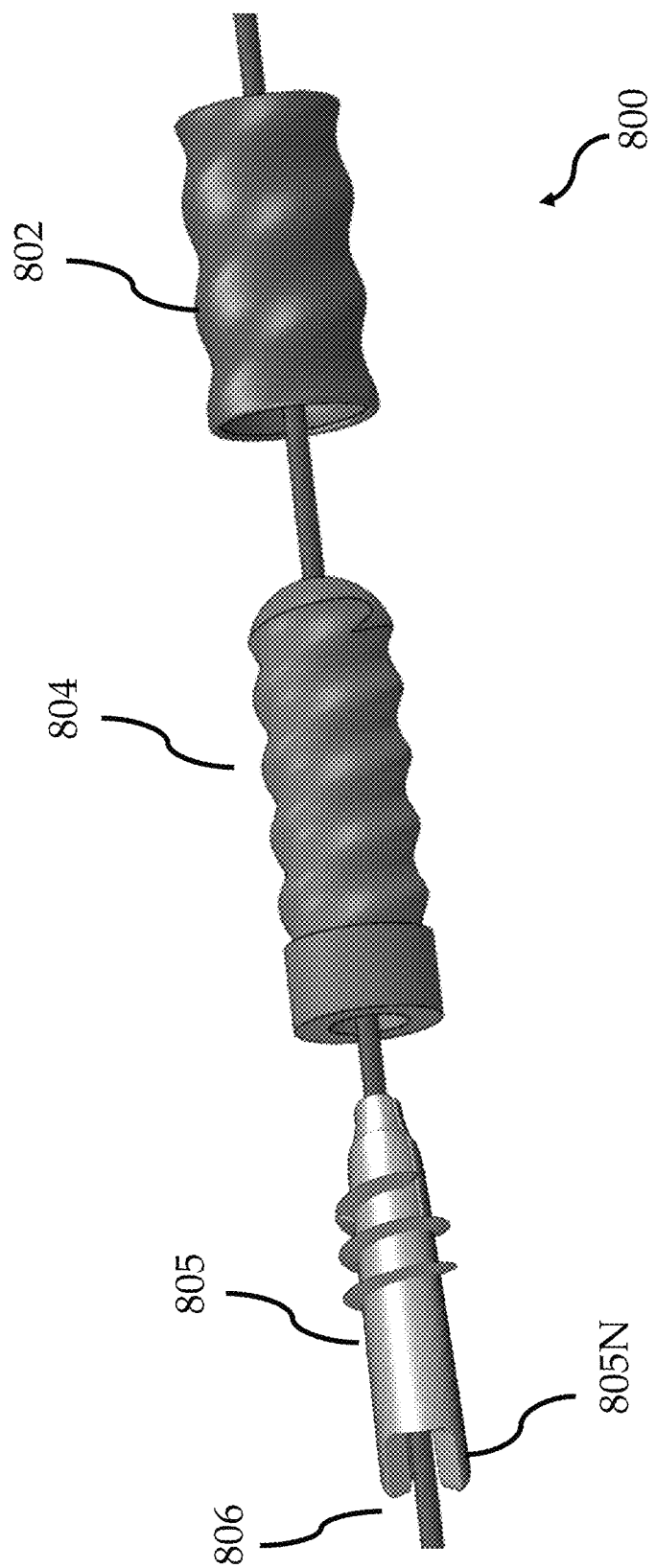
FIG. 8 is a perspective view of a system according to an embodiment.

FIG. 8 is a perspective view of a system 800 for driving a stent 802, according to an embodiment. System 800 includes stent 802, applicator 804, and torque connector 805 arranged around drive catheter 806. Torque connector 805 is configured to attach to a driver 806, such that rotation of the driver threadably engages torque connector 805 into inner wall of applicator 804. Similarly, applicator 804 threadably engages with stent 802. As shown in FIG. 8, rotation of drive catheter 806 can drive torque connector 805 and by extension applicator 804 and stent 802, after which drive catheter torque connector 805 and applicator 804 can be removed by driving those components in reverse, leaving stent 802 in an airway or other passage benefitting from added support. In various embodiments, system 800 can also include a guidewire as shown in FIG. 2. In alternative embodiments, torque applicator 805 can couple to driver 806 mechanically, chemically (e.g., by adhesion), or by any other coupling mechanism known to those of skill in the art.

Torque applicator 805 includes nubs 805N such that it can be gripped by a user. When the torque connector 805 is rotated by the user it can be advanced into applicator 804 to permanently couple it to applicator 804 and to the drive catheter (e.g. driver 108 of FIG. 1). Torque applicator 805 and applicator 804 can be rotated together by rotation of drive catheter 806 to move stent 802 and then be retracted, leaving stent 802 in place in an airway or other passage benefitting from added support.

In embodiments, a kit or package can be provided to a medical professional for introducing a stent such as those described above. For example, the kit could include a quantity of material for use in an additive manufacturing process. The kit could also include a guide wire and driving catheter, in embodiments, or other components that would be used to determine the size and shape of a patient's airway.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A stent comprising:
   a conformable body extending along a length;
   at least one ridge extending along an outer wall of the conformable body;
   at least one engagement feature arranged along an inner wall of the conformable body configured to engage with an adjacent component to advance the stent;
   wherein the stent is formed entirely of polymeric material that is conformable, biocompatible, and suitable for additive manufacturing.

2. The stent of claim 1 wherein the length and outer diameter are customized to a patient based upon a size of the patient's airway.

3. The stent of claim 1 wherein the polymeric material is silicone.

4. The stent of claim 1 wherein the ridge forms a screw thread pattern.

5. The stent of claim 2 wherein the ridge is one of a set of ridges each arranged along the outer wall of the conformable body, and wherein the set of ridges are arranged such that they correspond to anatomical features of the patient.

6. The stent of claim 1 wherein the engagement feature is a screw thread.

* * * * *